(12) United States Patent
Xu et al.

(10) Patent No.: US 9,828,634 B2
(45) Date of Patent: Nov. 28, 2017

(54) MARKERS FOR DIFFERENTIATION OF STEM CELLS INTO DIFFERENTIATED CELL POPULATIONS

(71) Applicant: REGENERATIVE MEDICAL SOLUTIONS, INC., Chicago, IL (US)

(72) Inventors: Xiaofang Xu, Park Ridge, IL (US); Jon Odorico, Park Ridge, IL (US); Erik Forsberg, Park Ridge, IL (US); Amber A. Mael, Madison, WI (US); Guy Tagliavia, Park Ridge, IL (US)

(73) Assignee: REGENERATIVE MEDICAL SOLUTIONS, INC., Chicago, IL (US)

( * ) Notice: Subject to any disclaimer, the term of this patent is extended or adjusted under 35 U.S.C. 154(b) by 0 days.

(21) Appl. No.: 15/004,188

(22) Filed: Jan. 22, 2016

(65) Prior Publication Data

US 2016/0230225 A1 Aug. 11, 2016

Related U.S. Application Data

(60) Provisional application No. 62/106,564, filed on Jan. 22, 2015.

(51) Int. Cl.
*C12N 5/00* (2006.01)
*C12Q 1/68* (2006.01)
*C12N 5/071* (2010.01)
*A61K 35/39* (2015.01)
*C12N 5/074* (2010.01)
*A61K 35/545* (2015.01)

(52) U.S. Cl.
CPC ............ *C12Q 1/6876* (2013.01); *A61K 35/39* (2013.01); *C12N 5/0676* (2013.01); *C12N 5/0696* (2013.01); *A61K 35/545* (2013.01); *C12N 2500/25* (2013.01); *C12N 2501/115* (2013.01); *C12N 2501/15* (2013.01); *C12N 2501/155* (2013.01); *C12N 2501/16* (2013.01); *C12N 2501/602* (2013.01); *C12N 2501/603* (2013.01); *C12N 2501/604* (2013.01); *C12N 2501/606* (2013.01); *C12N 2506/22* (2013.01); *C12N 2506/45* (2013.01); *C12N 2510/00* (2013.01); *C12Q 2600/158* (2013.01)

(58) Field of Classification Search
CPC ...................................................... A61K 35/39
USPC ......................................................... 435/325
See application file for complete search history.

(56) References Cited

U.S. PATENT DOCUMENTS

| | | | |
|---|---|---|---|
| 5,843,780 A | 12/1998 | Thomson et al. | |
| 6,071,691 A | 6/2000 | Hoekstra | |
| 7,951,592 B2 | 5/2011 | Chen et al. | |
| 8,058,065 B2 | 11/2011 | Yamanaka et al. | |
| 8,349,609 B2 | 1/2013 | Dealy et al. | |
| 8,546,140 B2 | 10/2013 | Mack et al. | |
| 8,852,941 B2 | 10/2014 | Osaka et al. | |
| 2006/0110830 A1 | 5/2006 | Dominko et al. | |
| 2009/0253588 A1 | 10/2009 | West et al. | |
| 2011/0002897 A1 | 1/2011 | Snyder et al. | |
| 2011/0200568 A1 | 8/2011 | Ikeda et al. | |
| 2011/0275105 A1 | 11/2011 | Wu et al. | |
| 2012/0128655 A1 | 5/2012 | Kim et al. | |
| 2012/0213746 A1 | 8/2012 | Rana | |
| 2013/0143321 A1 | 6/2013 | Saitou et al. | |
| 2013/0157358 A1 | 6/2013 | Su et al. | |
| 2013/0209421 A1* | 8/2013 | Efrat | C12N 5/0696 424/93.7 |
| 2013/0210141 A1 | 8/2013 | Rajesh et al. | |
| 2013/0259836 A1 | 10/2013 | Lee et al. | |
| 2013/0266541 A1 | 10/2013 | Zambidis et al. | |
| 2013/0345094 A1 | 12/2013 | Noggle et al. | |
| 2014/0289882 A1 | 9/2014 | Zhu et al. | |
| 2014/0329226 A1 | 11/2014 | Maione | |

FOREIGN PATENT DOCUMENTS

| | | |
|---|---|---|
| WO | WO0052145 | 9/2000 |
| WO | WO0100650 | 1/2001 |

OTHER PUBLICATIONS

Planello et al. (2014, Cell Regeneration, vol. 3(4), pp. 1-14).*
Nissenbaum et al., 2013, Stem Cell Reports, vol. 1, pp. 509-517.*
Iyashchenko et al. (2013, Am. J. Physiol. Heart Circ., vol. 305, pp. H913-H922).*
Amabile et al., "Induced pluripotent stem cells: current progress and potential for regenerative medicine." Trends Mol Med. Feb. 2009;15(2):59-68.
Assady et al., "Insulin Production by Human Embryonic Stem Cells" Diabetes Aug. 2001 vol. 50 No. 8 1691-1697.
Baker "Adult cells reprogrammed to pluripotency, without tumors" Nature Reports Stem Cells, Dec. 6, 2007, 3 pages.
Bar-Nur et al.,"Epigenetic memory and preferential lineage-specific differentiation in induced pluripotent stem cells derived from human pancreatic islet beta cells." Cell Stem Cell. Jul. 8, 2011;9(1):17-23.
Brolen et al., "Signals from the embryonic mouse pancreas induce differentiation of human embryonic stem cells into insulin-producing beta-cell-like cells." Diabetes. Oct. 2005;54(10):2867-74.
Khan et al., "Live cell imaging distinguishes bona fide human iPS cells from partially reprogrammed cells." Nat Biotechnol. Nov. 2009;27(11):1033-7.
D'Amour et al., "Efficient differentiation of human embryonic stem cells to definitive endoderm." Nat Biotechnol. Dec. 2005;23(12):1534-41.
Jonsson et al. "Insulin-promoter-factor 1 is required for pancreas development in mice" Nature 371, 606-609 (Oct. 13, 1994).
Karumbayaram et al., "Directed differentiation of human-induced pluripotent stem cells generates active motor neurons." Stem Cells. Apr. 2009;27(4):806-11.
Leech et al., "Expression of cAMP-regulated guanine nucleotide exchange factors in pancreatic beta-cells." Biochem Biophys Res Commun. Nov. 11, 2000;278(1):44-7.

(Continued)

*Primary Examiner* — Thaian N Ton
*Assistant Examiner* — David A Montanari
(74) *Attorney, Agent, or Firm* — Casimir Jones, S.C.

(57) ABSTRACT

Provided herein are systems and methods for identifying cell-specific differentiation markers. In particular, provided herein are systems and methods for generating induced pluripotent cells (IPS) from human cells, differentiating the IPS into differentiated cells, and identifying differentiation specific markers.

15 Claims, No Drawings

(56) References Cited

OTHER PUBLICATIONS

Moad et al., "A novel model of urinary tract differentiation, tissue regeneration, and disease: reprogramming human prostate and bladder cells into induced pluripotent stem cells." Eur Urol. Nov. 2013;64(5):753-61.

Mummery et al., "Differentiation of human embryonic stem cells and induced pluripotent stem cells to cardiomyocytes: a methods overview." Circ Res. Jul. 20, 2012;111(3):344-58.

Pagliuca et al., "Generation of functional human pancreatic β cells in vitro." Cell. Oct. 9, 2014;159(2):428-39.

Rajagopal et al., "Insulin staining of ES cell progeny from insulin uptake." Science. Jan. 17, 2003;299(5605):363.

Rezania et al., "Reversal of diabetes with insulin-producing cells derived in vitro from human pluripotent stem cells." Nat Biotechnol. Nov. 2014;32(11):1121-33.

Schuldiner et al., "Effects of eight growth factors on the differentiation of cells derived from human embryonic stem cells." Proc Natl Acad Sci U S A. Oct. 10, 2000;97(21):11307-12.

Segev et al., "Differentiation of human embryonic stem cells into insulin-producing clusters." Stem Cells. 2004;22(3):265-74.

Sipione et al., "Insulin expressing cells from differentiated embryonic stem cells are not beta cells." Diabetologia. Mar. 2004;47(3):499-508.

Takahashi et al., "Induction of pluripotent stem cells from adult human fibroblasts by defined factors." Cell. Nov. 30, 2007;131(5):861-72.

Takahashi et al., "Induction of pluripotent stem cells from mouse embryonic and adult fibroblast cultures by defined factors." Cell. Aug. 25, 2006;126(4):663-76.

Takeuchi et al., "Endodermal differentiation of human pluripotent stem cells to insulin-producing cells in 3D culture." Sci Rep. Mar. 27, 2014;4:4488.

Tanaka, et. Al., Proc Natl Acad Sci U S A. Sep. 14, 1999;96(19):10857-62.

Theunissen et al., "Systematic identification of culture conditions for induction and maintenance of naive human pluripotency." Cell Stem Cell. Oct. 2, 2014;15(4):471-87.

Wang et al., "Primate-specific endogenous retrovirus-driven transcription defines naive-like stem cells." Nature. Dec. 18, 2014;516(7531):405-9.

Lu, Xinyi et al., "The retrovirus HERVH is a long noncoding RNA required for human embryonic stem cell identity." Nat Struct Mol Biol. Apr. 2014;21(4):423-5.

Yu et al., "Induced pluripotent stem cell lines derived from human somatic cells." Science. Dec. 21, 2007;318(5858):1917-20.

Zhou et al., "Generation of human induced pluripotent stem cells from urine samples." Nat Protoc. Dec. 2012;7(12):2080-9.

Zhou et al., "Generation of induced pluripotent stem cells using recombinant proteins." Cell Stem Cell. May 8, 2009;4(5):381-4.

International Search Report dated Mar. 30, 2016, for co-pending international application No. PCT/US2016/014460 filed Jan. 22, 2016. 16 pages.

* cited by examiner

_US 9,828,634 B2_

MARKERS FOR DIFFERENTIATION OF STEM CELLS INTO DIFFERENTIATED CELL POPULATIONS

The present Application claims priority to U.S. Provisional Patent Application Ser. No. 62/106,564 filed Jan. 22, 2015, the disclosure of which is herein incorporated by reference in its entirety

FIELD

Provided herein are systems and methods for identifying cell-specific differentiation markers. In particular, provided herein are systems and methods for generating induced pluripotent cells (IPS) from human cells, differentiating the IPS into differentiated cells, and identifying differentiation specific markers.

BACKGROUND

Type I diabetes is an autoimmune disease of humans caused by destruction of pancreatic islet β cells. Transplantations of whole pancreas or isolated islet cells are effective treatments for Type I diabetes to restore insulin independence, when combined with immunosuppressive therapy. Successful transplantation of isolated islets from human cadaver donors is a proof-in-principle that a cell-based therapy for human diabetes can be successful. However, the lack of available organs and islet cells has restricted this therapy to very few patients. The amount of islet cells which can be harvested from human cadavers is extremely limited. Therefore, technologies capable of producing significant quantities of cells of the pancreatic lineage are highly desirable.

Stem cells are cells that are capable of differentiating into many cell types. Embryonic stem cells are derived from embryos and are potentially capable of differentiation into all of the differentiated cell types of a mature body. Certain types of stem cells are "pluripotent," which refers to their capability of differentiating into many cell types. One type of pluripotent stem cell is the human embryonic stem cell (hESC), which is derived from a human embryonic source. Human embryonic stem cells are capable of indefinite proliferation in culture, and therefore, are an invaluable resource for supplying cells and tissues to repair failing or defective human tissues in vivo.

Similarly, induced pluripotent stem (iPS) cells, which may be derived from non-embryonic sources, can proliferate without limit and differentiate into each of the three embryonic germ layers. It is understood that iPS cells behave in culture essentially the same as ESCs. Human iPS cells and ES cells express one or more pluripotent cell-specific markers, such as Oct-4, SSEA-3, SSEA-4, Tra 1-60, Tra 1-81, and Nanog (Yu et al. Science, Vol. 318. No. 5858, pp. 1917-1920 (2007); herein incorporated by reference in its entirety). Also, recent findings of Chan, suggest that expression of Tra 1-60, DNMT3B, and REX1 can be used to positively identify fully reprogrammed human iPS cells, whereas alkaline phosphatase, SSEA-4, GDF3, hTERT, and NANOG are insufficient as markers of fully reprogrammed human iPS cells. (Chan et al., Nat. Biotech. 27:1033-1037 (2009); herein incorporated by reference in its entirety). Subsequent references herein to hESCs and the like are intended to apply with equal force to iPS cells.

Under nonselective culture conditions, it has been previously demonstrated that a wide variety of stem cells, including mouse embryonic stem cells and hESCs, differentiate spontaneously into cells of many lineages including the pancreatic lineage. Such differentiated cells can express the pancreatic duodenal homeobox 1 (PDX1) gene, a transcription factor specifying the pancreatic lineage, and can also express insulin. However, without selective conditions, stem cells will spontaneously and simultaneously differentiate in the same culture dish into a wide variety of different lineages with only a small proportion of the cells being differentiated towards any particular lineage.

Culture systems that allow the spontaneous differentiation of hESCs into insulin-staining cells have been reported (Assady, S. et al., Insulin production by human embryonic stem cells. Diabetes 50, 1691-1697 (2001); and Segev, H. et al., Differentiation of human embryonic stem cells into insulin-producing clusters. Stem Cells 22, 265-274 (2004); herein incorporated by reference in their entireties). However, these studies neither investigated endoderm marker expression nor demonstrated development of cells possessing stereotypical characteristics of β cells: simultaneous expression of insulin and PDX1, which is required for pancreas formation and co-activates the insulin promoter (Jonsson, J. et al., Insulin-promoter-factor 1 is required for pancreas development in mice. Nature 371, 606-609 (1994); herein incorporated by reference in its entirety). Because non-β cells such as neuronal cells, may express insulin (Sipione, S. et al., Insulin expressing cells from differentiated embryonic stem cells are not β cells. Diabetologia 47, 499-508 (2004); herein incorporated by reference in its entirety), and insulin present in the culture media may be taken up into other cell types under certain conditions in vitro (Rajagopal, J. et al., Insulin staining of ES cell progeny from insulin uptake. Science 299, 363 (2003); herein incorporated by reference in its entirety), it is important that the endoderm and pancreatic origin of insulin-staining cells derived from hESCs be ascertained.

Spontaneous differentiation of hESCs has produced PDX1$^+$/FOXA2$^+$ cells and co-transplantation of these differentiated cells with mouse dorsal pancreas (E13.5) produced PDX1$^+$/insulin$^+$ cells, and co-staining of insulin and C-peptide was observed (Brolen, G. K. et al., Signals from the embryonic mouse pancreas induce differentiation of human embryonic stem cells into insulin-producing β-cell-like cells. Diabetes 54, 2867-2874 (2005); herein incorporated by reference in its entirety). Thus, pancreatic lineage cells can be induced from spontaneously differentiating hESCs by signals emanating from the embryonic pancreas. However, the experimental methods used to reach such observations would be impractical to adopt into a high-throughput culture protocol. Moreover, the nature of the molecular signals was not revealed by the study. In addition, unselected stem cell populations are often tumorigenic, meaning that they will generate non-malignant tumors, known as teratomas, in immunodeficient animals like undifferentiated ES cells do.

Several studies have evaluated the effects of growth factors on hESC differentiation to endoderm (Schuldiner, M. et al., Effects of eight growth factors on the differentiation of cells derived from human embryonic stem cells. Proc Natl Acad Sci USA 97, 11307-11312 (2000) and D'Amour, K. A. et al. Efficient differentiation of human embryonic stem cells to definitive endoderm. Nat. Biotechnol. 23, 1534-1541 (2005); herein incorporated by reference in their entireties). However, highly efficient differentiation to pancreatic precursors and islet cells has not been achievable. Furthermore, insulin producing cells generated using previously reported methods are less responsive to glucose, in that, they appear less functionally mature than adult human β cells and are believed to possess a phenotype more like immature β cells.

SUMMARY

Provided herein are systems and methods for identifying cell-specific differentiation markers. In particular, provided herein are systems and methods for generating induced pluripotent cells (IPS) from human cells, differentiating the IPS into differentiated cells, and identifying differentiation specific markers.

For example, in some embodiments, the present disclosure provides a method of identifying differentiation markers, comprising: a) culturing a primary cell under conditions such that the primary cell de-differentiates to generate an induced pluripotent stem cell (iPSC); b) treating the iPSC under conditions such that the iPSC differentiates into a differentiated cell; and c) identifying molecular markers that are indicative of differentiation into the differentiated cell. In some embodiments, the iPSC is in a naïve state. In some embodiments, the primary cell is a pancreatic beta cell. In some embodiments, the differentiated cell is a pancreatic beta cell. In some embodiments, the primary and differentiated cell are the same or different cell type. In some embodiments, the culturing comprises expanding the cell. In some embodiments, the culturing comprises inducing expression of one or more genes selected from, for example, Oct4 (Pou5f1), Sox2, cMyc, nanog, LIN28, Glis1, or Klf4. In some embodiments, the treating comprises the steps of (a) culturing the iPSCs in a chemically defined medium, fibroblast growth factor, Activin A, and bone morphogenetic protein; (b) culturing the cells from step (a) in the presence of chemically defined medium comprising insulin, transferrin, and selenium, a fibroblast growth factor and nicotinamide; (c) culturing the cells from step (b) in the presence of a chemically defined medium comprising insulin, transferrin, and selenium; retinoic acid; a bone morphogenetic protein inhibitor; and nicotinamide; and (d) culturing the cells from step (c) in the presence of a serum-free medium, an insulin-like growth factor, insulin, nicotinamide, exendin-4 and/or GLP-1, a TGF-β inhibitor, and an agent that increase cAMP. In some embodiments, the method further comprises (e) maintaining the cells of the pancreatic lineage for 1-50 days by culturing the cells from step (d) in the presence of a serum-free medium, an insulin-like growth factor, fibroblast growth factor, insulin, nicotinamide, exendin-4 and/or GLP-1, and an agent that increase cAMP. In some embodiments, the fibroblast growth factor of step (a) is basic fibroblast growth factor (bFGF). In some embodiments, the bone morphogenetic protein of step (a) is BMP4. In some embodiments, the chemically defined medium comprising insulin, transferrin, and selenium of steps (b) and/or step (c) is ITS medium. In some embodiments, the fibroblast growth factor of step (b) and/or step (d) is FGF7. In some embodiments, the bone morphogenetic protein inhibitor of step (c) is a BMP4 inhibitor. In some embodiments, the BMP4 inhibitor is Noggin. In some embodiments, the serum-free medium of step (d) is B27. In some embodiments, the insulin-like growth factor comprises IGF I and IGF II. In some embodiments, step (d) comprises culturing in exendin-4. In some embodiments, a TGF-β inhibitor comprises ALK5i II. In some embodiments, step (d) comprises culturing in forskolin. In some embodiments, step (a) has a duration of 2-10 days. In some embodiments, the identifying comprises sequencing expressed genes in the primary cell, the iPSC, and the differentiated cell and comparing the expressed genes to identify gene expression markers indicative of differentiation into the differentiated cell. For example, in some embodiments, gene expression levels, protein levels, or metabolite levels between the primary cells, the de-differentiated iPSC, the differentiated cell, or any intermediate stage are compared. In some embodiments, sequencing, RT-PCR, mass spec, chromatography, or hybridization methods are used to compare levels of gene expression, protein expression, or metabolite levels. In some embodiments, the comparing comprises use of bioinformatics methods.

Also provided are one or more differentiation markers identified by the methods described herein.

Additional embodiments provide the use of the markers to identify differentiated cells.

In some embodiments, provided herein is a method of testing a library of compounds for effect on differentiation of iPSCs, comprising: (a) receiving a plurality of reaction vessels, each vessel containing differentiated cells or iPSCs; (b) exposing each of the plurality of reaction vessels to a compound from the library of compounds; and (c) detecting the effect of the compounds on the expression of the markers described herein.

Further embodiments provide a method of monitoring differentiation of iPSCs, comprising: a) contacting iPSCs with conditions that induce differentiation into a differentiated cell; and b) identifying expression of the markers described herein. In some embodiments, the identifying step is repeated two or more times during the contacting.

Additional embodiments provide therapeutic methods and uses, comprising providing (e.g., transplanting) a differentiated cell (e.g., beta cell) that exhibits markers described herein to a subject in need thereof. In some embodiments, the differentiated cell exhibits a marker profile indicative of a "therapeutically suitable cell" (e.g., a cell that is efficacious for the intended purpose (e.g., secretes insulin) and non-cancerous). In some embodiments, the method further comprises the step of analyzing the cell for other desired traits (e.g., immunocompatibiliy).

Additional embodiments are described herein.

Definitions

As used herein the term "stem cell" ("SC") refers to cells that can self-renew and differentiate into multiple lineages. A stem cell is a developmentally pluripotent or multipotent cell. A stem cell can divide to produce two daughter stem cells, or one daughter stem cell and one progenitor ("transit") cell, which then proliferates into the tissue's mature, fully formed cells. Stem cells may be derived, for example, from embryonic sources ("embryonic stem cells") or derived from adult sources. For example, U.S. Pat. No. 5,843,780 to Thompson describes the production of stem cell lines from human embryos. PCT publications WO 00/52145 and WO 01/00650 describe the use of cells from adult humans in a nuclear transfer procedure to produce stem cell lines.

Examples of adult stem cells include, but are not limited to, hematopoietic stem cells, neural stem cells, mesenchymal stem cells, and bone marrow stromal cells. These stem cells have demonstrated the ability to differentiate into a variety of cell types including adipocytes, chondrocytes, osteocytes, myocytes, bone marrow stromal cells, and thymic stroma (mesenchymal stem cells); hepatocytes, vascular cells, and muscle cells (hematopoietic stem cells); myocytes, hepatocytes, and glial cells (bone marrow stromal cells) and, indeed, cells from all three germ layers (adult neural stem cells).

As used herein, the term "totipotent cell" refers to a cell that is able to form a complete embryo (e.g., a blastocyst).

As used herein, the term "pluripotent cell" or "pluripotent stem cell" refers to a cell that has complete differentiation versatility, e.g., the capacity to grow into any of the mammalian body's approximately 260 cell types. A pluripotent cell can be self-renewing, and can remain dormant or quiescent within a tissue. Unlike a totipotent cell (e.g., a fertilized, diploid egg cell), a pluripotent cell, even a pluripotent embryonic stem cell, cannot usually form a new blastocyst.

As used herein, the term "induced pluripotent stem cells" ("iPSCs") refers to a stem cell induced from a somatic cell, e.g., a differentiated somatic cell, and that has a higher potency than said somatic cell. iPS cells are capable of self-renewal and differentiation into mature cells.

As used herein, the term "multipotent cell" refers to a cell that has the capacity to grow into a subset of the mammalian body's approximately 260 cell types. Unlike a pluripotent cell, a multipotent cell does not have the capacity to form all of the cell types.

As used herein, the term "progenitor cell" refers to a cell that is committed to differentiate into a specific type of cell or to form a specific type of tissue.

As used herein, the term "embryonic stem cell" ("ES cell" or "ESC") refers to a pluripotent cell that is derived from the inner cell mass of a blastocyst (e.g., a 4- to 5-day-old human embryo), and has the ability to yield many or all of the cell types present in a mature animal.

As used herein the term "feeder cells" refers to cells used as a growth support in some tissue culture systems. Feeder cells may be embryonic striatum cells or stromal cells.

As used herein, the term "chemically defined media" refers to culture media of known or essentially-known chemical composition, both quantitatively and qualitatively. Chemically defined media is free of all animal products, including serum or serum-derived components (e.g., albumin).

As used herein, the term "serum-free media" refers to culture media that is devoid of serum, but not necessarily of other undefined components.

As used herein, the terms "pancreatic lineage cells" or "cells of the pancreatic lineage" refer to any endocrine (e.g., alpha cells, beta cells, delta cells, PP cells, epsilon cells, etc.) or exocrine cells that comprise the pancreas, or the precursor cells (e.g., progenitor cells, intermediate development cells, etc.) that are committed to a pancreatic cell lineage.

As used herein, the terms "pancreatic beta cells," "islet beta cells," or "beta cells" refer to monohormonal, pancreatic lineage, endocrine cells located in the islets of Langerhans of the pancreas. Beta cells are capable of secreting insulin in response to elevated glucose concentrations (e.g., glucose-responsive) and express markers, including, but not limited to, insulin and pdx1.

As used herein, the terms "beta-like cells" or "induced beta cells" refer to cells generated from pluripotent stem cells by human manipulation that exhibit characteristics of beta cells, including, but not limited to, glucose responsiveness, insulin secretion, monohormonal, and/or expressing beta cell markers (e.g., insulin, PDX1). In some embodiments, beta-like cells are characterized based on their similarity, in terms of a particular characteristic, to beta cells (e.g., from cadaver). For example, a particular group of beta-like cells may exhibit >90% glucose responsiveness, >75% pdx1 expression, >110% insulin secretion, etc.

As used herein, the term "therapeutically suitable cell" refers to a differentiated cell that exhibits a marker profile (e.g., the markers described herein) that are indicative of a differentiated cell that is efficacious for the intended purpose (e.g., secretes insulin) and safe (e.g., non-cancerous)). In some embodiments, the cell is further analyzed for other desired traits (e.g., immunocompatibiliy).

DETAILED DESCRIPTION

Provided herein are systems and methods for identifying cell-specific differentiation markers. In particular, provided herein are systems and methods for generating induced pluripotent cells (IPS) from human cells, differentiating the IPS into differentiated cells, and identifying differentiation specific markers.

While a variety of research groups have worked on differentiating pluripotent cells into beta cells, it remains difficult to determine when cells are properly differentiated (See e.g., Kushner et al., Cell Stem Cell 15, Nov. 6, 2014; herein incorporated by reference in its entirety). The systems and methods described herein find use in the identification of markers useful in the development of differentiated cells (e.g. insulin producing cells) from pluripotent cells (e.g., IPS). The markers and differentiated cells find use in research, screening, and therapeutic uses.

In some embodiments, the present disclosure provides systems and methods for iteratively analyzing the transcriptome or other cellular or metabolic properties (e.g., proteome, genomic variations, metabolic variations) of one or more developmental stages during the conversion of iPSCs to differentiated cells (e.g., beta-like cells using cells from "normal" and diabetic (esp. MODY patients) donors). In some embodiments, the results (e.g., markers) from differentiated cells are compared to the normal (e.g., normal beta cells such as the starting population). In some embodiments, markers are used to improve the differentiation process, for drug screening, and to identify differentiated cells.

In some embodiments, the phenotype of differentiated (e.g., beta-like cells) made from iPSCs originally derived from beta cells is compared to those derived from other tissues (e.g., skin, blood) from the same patient. In some embodiments, these results are also iteratively compared to the transcriptome or other measure of donor beta cells.

The systems and methods described herein utilize the following steps, each of which are discussed in detail below: 1) obtain primary donor cells (e.g., from a human or non-human animal donor); 2) de-differentiate the donor cells into induced pluripotent cells (iPSCs); 3) differentiate said iPSCs into differentiated cells; and 4) determine a cellular phenotype (e.g., transcriptome) of two or more of the donor cells, the iPSCs, and the differentiated cells.

I. Donor Cells and De-Differentiation

The present disclosure is not limited to particular donor cells. In some embodiments, donor cells are derived from a human or other animal donor. Examples of donor cells include, but are not limited to, trichocyte, keratinocyte, gonadotrope, corticotrope, thyrotrope, somatotrope, lactotroph, neuron, glia (Schwann cell), satellite glial cell, chromaffin cell, parafollicular cell, glomus cell, melanocyte, nevus cell, merkel cell, odontoblast, cementoblast, corneal keratocyte, oligodendrocyte astrocyte, ependymocytes, pinealocyte, pneumocyte, clara cell, goblet cell, G cell, D cell, ECL cell, gastric chief cell, parietal cell, foveolar cell, K cell, S cell, D cell, I cell, paneth cell, microfold cell, hepatocyte, hepatic stellate cell, cholecystocyte, centroacinar cell, pancreatic stellate cell, alpha cell, beta cell, delta cell, F cell, epsilon cell, follicular cell, parathyroid chief cell, oxyphil cell, urothelial cells, osteoblast, osteocyte, chondroblast, chondrocyte, myofibroblast, fibroblast, fibrocyte, myoblast, myocyte, myosatellite cell, tendon cell, cardiac muscle cell, lipoblast, adipocyte, red blood cells, white blood cells, interstitial cell of Cajal, angioblast, endothelial cell, mesangial cell, juxtaglomerular cell, macula densa cell, stromal cell, interstitial cell, telocytes, simple epithelial cell, podocyte, sertoli cell, leydig cell, granulosa cell, peg cell, spermatozoon, ovum, lymphocytes, myeloid cells, angioblast/mesoangioblast, pericyte, Mural cell, etc. In some exemplary embodiments, the present disclosure is illustrated with pancreatic beta cells, although other cells types are contemplated. In some embodiments, cells are obtained from an autologous or non-autologous source (e.g. cadaver or live donor).

Donor cells are de-differentiated into iPSCs using any suitable method. In some embodiments, the methods described in U.S. Pat. App. No. 20130209421 (herein incorporated by reference in its entirety) are utilized. In some embodiments, cells are first dispersed into a single cell suspension (e.g., by the addition of trypsin or by trituration). In some embodiments, cells are then expanded for a period of time (e.g., about two weeks, about three weeks, about four weeks, about five weeks, about six weeks, about seven weeks, about eight weeks, about nine weeks, about 10 weeks, about 11 weeks, about 12 weeks, about 13 weeks, about 14 weeks, about 15 weeks or even about 16 weeks) in a medium (e.g., serum free medium). The medium used to culture and expand cell may further comprise supplementary constituents which may improve growth and/or viability thereof. These include, but are not limited to, growth factors (e.g. hepatocyte growth factor, nerve growth factor and/or epidermal growth factor) serum (e.g. fetal calf serum or fetal bovine serum), glucose, and antibiotics.

In some embodiments, iPSCs are induced by induction of one or more genes (e.g., including but not limited to, Oct4 (Pou5f1), Sox2, cMyc, nanog, LIN28, Glis1, and Klf4). Expression of such genes is induced using any suitable method (e.g., by delivering exogenous copies of genes using viral delivery systems, chemical induction, and microRNA induced induction).

Exemplary methods for generating iPSCs are described, for example, in Takahashi, K; Yamanaka, S (2006). Cell 126 (4): 663-76. Zhou H, Wu S, Joo J Y, et al. (May 2009). Cell Stem Cell 4 (5): 381-4. Moad, Mohammad; Pal, Deepali; Hepburn, Anastasia C; Williamson, Stuart C; Wilson, Laura; Lako, Majlinda; Armstrong, Lyle; Hayward, Simon W; Franco, Omar E; Cates, Justin M; Fordham, Sarah E; Przyborski, Stefan; Carr-Wilkinson, Jane; Robson, Craig N; Heer, Rakesh (2013). European Urology 64 (5): 753-761 Baker, Monya (2007-12-06) Nature Reports Stem Cells; Yu J, Vodyanik M A, et al. (2007) Science 318 (5858): 1917-1920; Takahashi K, et al. (2007). Cell 131 (5): 861-872; Zhou, Ting; Benda, Christina; Dunzinger, Sarah; Huang, Yinghua; Ho, Jenny Cy; Yang, Jiayin; Wang, Yu; Zhang, Ya; Zhuang, Qiang; Li, Yanhua; Bao, Xichen; Tse, Hung-Fat; Grillari, Johannes; Grillari-Voglauer, Regina; Pei, Duanqing; Esteban, Miguel A (7 Nov. 2012). Nature Protocols 7 (12): 2080-2089; U.S. Pat. App. Nos 20110200568, US20130345094A1, US20120213746, US20120128655, US20130266541, US20110275105, and U.S. Pat. No. 8,058, 065 8,852,941 and 8,546,140; each of which is herein incorporated by reference in its entirety.

In some embodiments, human pluripotent cells are reverted to a "naive" state that removes tissue specific epigenetic marks See e.g., Wang, et. al. Nature, Dec. 18-Dec. 25, 2014, Vol. 516(7531), pp. 405-409T; Xinyi et al., Nature Structural & Molecular Biology, 2014, Vol. 21(4), p. 423; and Theunissen T W et al., Cell Stem Cell. 2014 Oct. 2; 15(4):471-87. Epub 2014 Jul. 24; each of which is herein incorporated by reference in its entirety.

II. Differentiation of iPSCs

Following generation of iPSCs, the iPSCs are differentiated into a specific cell type. In some embodiments, the iPSCs are differentiated into the same cell type as the primary cell that was used to generate iPSCs. In other embodiments, iPSCs are differentiated into a different cell type that the primary progenitor cell type. The present disclosure is not limited to differentiation of iPSCs into a particular cell type. In some embodiments, insulin generating pancreatic beta cells are generated, although the disclosure is not limited to a beta cells.

Examples of differentiated cells include, but are not limited to, trichocyte, keratinocyte, gonadotrope, corticotrope, thyrotrope, somatotrope, lactotroph, neuron, glia (Schwann cell), satellite glial cell, chromaffin cell, parafollicular cell, glomus cell, melanocyte, nevus cell, merkel cell, odontoblast, cementoblast, corneal keratocyte, oligodendrocyte astrocyte, ependymocytes, pinealocyte, pneumocyte, clara cell, goblet cell, G cell, D cell, ECL cell, gastric chief cell, parietal cell, foveolar cell, K cell, S cell, D cell, I cell, paneth cell, microfold cell, hepatocyte, hepatic stellate cell, cholecystocyte, centroacinar cell, pancreatic stellate cell, alpha cell, beta cell, delta cell, F cell, epsilon cell, follicular cell, parathyroid chief cell, oxyphil cell, urothelial cells, osteoblast, osteocyte, chondroblast, chondrocyte, myofibroblast, fibroblast, fibrocyte, myoblast, myocyte, myosatellite cell, tendon cell, cardiac muscle cell, lipoblast, adipocyte, red blood cells, white blood cells, interstitial cell of Cajal, angioblast, endothelial cell, mesangial cell, juxtaglomerular cell, macula densa cell, stromal cell, interstitial cell, telocytes, simple epithelial cell, podocyte, sertoli cell, leydig cell, granulosa cell, peg cell, spermatozoon, ovum, lymphocytes, myeloid cells, angioblast/mesoangioblast, pericyte, Mural cell, etc.

The present disclosure is not limited to a particular method of differentiating iPSCs. In some exemplary embodiments, beta cells are generated using the method described in Provisional Patent Application No. 62/052,894, filed Sep. 19, 2014 and U.S. patent application Ser. No. 14/858,465, filed Sep. 18, 2015; each of which is herein incorporated by reference in its entirety.

In some embodiments, methods are provided for directed in vitro differentiation of pluripotent stem cells into beta cells. In some embodiments, the methods involve culturing the stem cells in the presence of an effective amount of the appropriate factors/reagents (e.g., fibroblast growth factor (e.g., bFGF, etc.), Activin A, and bone morphogenetic protein (e.g., BMP4) to induce differentiation, resulting in primitive streak and definitive endodermal cells. In some embodiments, these cells are subsequently cultured in the presence of an effective amount of the appropriate factors/reagents (e.g., ITS, FGF7, nicotinamide, etc.; ITS, Noggin, nicotinamide, retinoic acid, etc.) to result in the formation of progenitor foregut cells. In some embodiments, these progenitor foregut cells are further cultured in the presence of an effective amount of the appropriate factors/reagents (e.g., IGF I, IGF II, B27, nicotinamide, exendin-4, forskolin, Alk5i II, insulin, etc.) to result in the formation of pancreatic lineage endocrine cells (e.g., β cells). By utilizing defined medium components that promote pancreatic cell differentiation, the described methods provide a simple, reproducible approach to enable large-scale production of pancreatic cell types (e.g., β cells) for research, diagnostic, and/or therapeutic uses. In some embodiments, one or more culture steps are performed on Matrigel or the like.

Various growth factors and other chemical signals may initiate differentiation of iPSCs into progeny cell cultures of one or more particular lineage (e.g., beta-like cells or a cell population comprising beta-like cells).

One of these differentiation factors is known as bone morphogenetic protein (BMP). BMPs are members of the transforming growth factor-β (TGFβ) superfamily of secreted signaling molecules, which play extensive pleiomorphic roles in almost all aspects of embryonic development. BMP4 and other BMP family members, such as BMP2, BMP5, and BMP7, bind BMP type II receptor BRII, which recruits type I receptor BR1A (ALK3) or BR1B (ALK6). Upon ligand activation, the intracellular kinase domain of the type I receptors phosphorylates Smad1, -5, and -8, which are then escorted by a common Smad4 to enter the nucleus and activate target genes. The relative expression level of BMPs, receptors, and Smads within the cell is an important determinant of BMP-induced responses. BMP signaling, and disruption thereof by BMP inhibitors, affects the body plan of developing embryos. For example, along with activin, BMP4 synergistically promote formation of definitive endoderm in human embryonic stem cells. Subsequently, blocking of BMP4 action by BMP4 inhibitors favors pancreatic lineage differentiation over, for example liver induction. Known BMP4 inhibitors include Noggin, chordin, follistatin, Smad6, Smad7, Gremlin, Sog (short gastrulation), DAN (differential screening-selected gene aberrant in neuroblastoma), Cerberus, Dante and PRDC (Protein Related to DAN and Cerberus), LDN193189, and dorsomorphin.

Fibroblast growth factor (FGF) also plays a role in mesoderm formation. There are several different FGF subfamilies, the member ligands of which include FGF1-FGF23. Of the known FGF ligands, all show some degree of overlap of receptor binding, with the exception of FGF11-FGF14. (FGF Signaling in Vertebrate Development. Pownall M E, Isaacs H V. San Rafael (Calif.): Morgan & Claypool Life Sciences; 2010; herein incorporated by reference in its entirety).

Transforming growth factor beta (TGF-β) is a protein that controls proliferation, cellular differentiation, and other functions in most cells. TGF-β is part of a superfamily of proteins known as the transforming growth factor beta superfamily, which includes inhibins, anti-mullerian hormone, activin, bone morphogenetic protein, decapentaplegic and Vg-1 and TGF-β. The TGF-β signaling pathway is involved in many cellular processes in both adult organisms and the developing embryos, including cell growth, cell differentiation, apoptosis, cellular homeostasis and other cellular functions. In the TGFβ signaling pathway, a TGFβ superfamily ligand binds to a type II receptor, which recruits and phosphorylates a type I receptor. The type I receptor then phosphorylates receptor-regulated SMADs (R-SMADs) which binds a coSMAD. R-SMAD/coSMAD complexes then accumulate in the nucleus where they act as transcription factors and participate in the regulation of target gene expression. The cellular effect of TGF-β and other TGF-β superfamily members is regulated by inhibitors. Known TGF-β inhibitors include ALK5i, ALK5i II, GW-6004, A 83-01, D 4476, GW 788388, LY 365947, RepSox, SB 431542, SB 525334, SD 208, etc. (See, e.g., Tocris Bioscience).

Activin is a member of the TGF-β superfamily and has various effects on diverse biological systems (Abe Y, et al. Growth Factors 2004 June; 22(2):105-10; herein incorporated by reference in its entirety). Activin A has been reported to have a role in the induction of definitive endoderm from hESCs (D'Amour, K. A., et al. (2005); herein incorporated by reference in its entirety). However, results testing Activin A (at 5 ng/ml, 50 ng/ml, or 100 ng/ml) in serum-free medium indicate that this treatment alone cannot induce pancreatic cell differentiation.

Adenyl cyclase catalyzes the conversion of ATP to 3',5'-cyclic AMP (cAMP) and pyrpphosphate. Experiments have indicated that increased cAMP levels play a role in regulation of pancreatic beta-cell growth and differentiation (Leech et al. Biochem Biophys Res Commun. 2000 Nov. 11; 278(1):44-7; herein incorporated by reference in its entirety). Agonists of the adenyl cyclase system are agents that result in increased levels of cAMP, by directly acting upon adenyl cyclase (e.g., forskolin or other adenyl cyclase agonists), or by acting upstream of adenyl cyclase (e.g., glucagon binding to the glucogon receptor results in a conformational change in the receptor, activation of G-proteins, and the subsequent activation of adenyl cyclase).

A phosphodiesterase (PDE) is any enzyme that breaks a phosphodiester bond; specifically a cyclic nucleotide phosphodiesterase is an enzyme that degrades the phosphodiester bond in the second messenger molecules cAMP and cGMP. Inhibitors of cyclic nucleotide phosphodiesterases prevent degradation of cAMP and/or cGMP, thereby increasing the concentration of cAMP and/or cGMP in a system or solution or prolonging the effect of cAMP and/or cGMP. For example, methylated xanthenes (e.g., caffeine, aminophylline, IBMX, paraxanthine, pentoxifylline, theobromine, theophylline, etc.) inhibit cyclic nucleotide phosphodiesterases that degrade cAMP and/or cGMP, thereby increasing intracellular cAMP and/or cGMP concentration and activating cAMP- and/or cGMP dependent enzymes and pathways.

A concern in the culture of human ES cells is to remove, to the extent possible, undefined constituents and constituents of animal origin from ES cell culture conditions. Standardizing culture conditions minimizes the normal variations in biological materials to which the cells are exposed. Further, by avoiding the use of materials, cells, exudates or constituents of animal origin, one can avoid possible cross-species viral transmission through the culture system. Thus, utilization of chemically defined media (CDM) that avoid the use of animal products provides a baseline culture condition upon which differentiation factors may be added with predictable effects.

CDM may include a basal medium containing salts, vitamins, glucose and amino acids. The basal medium can be any of a number of commercially available media. For example, a combination of Dulbecco's Modified Eagle Medium and Hams F12 medium, sold as a combination (DMEM/F12; Invitrogen) may be utilized. To that combination may be added glutamine, β-mercaptoethanol, and non-essential amino acids. Other possible additives include antioxidants such as glutathione, N-acetyl-L-cysteine, vitamin C, vitamin E and lipids (TANAKA, et. Al., Proc Natl Acad Sci USA. 1999 Sep. 14; 96(19):10857-62; herein incorporated by reference in its entirety). A protein constituent of the medium is a serum substitute product. Albumin or purified albumin products, like the commercial product ALBUMAX (Invitrogen) may be used. Alternatively or in addition, a defined protein product made up of albumin, insulin and transferrin may be used. Human proteins are preferred but not essential so long as uncharacterized animal products are excluded.

FAB medium, for example, includes FGF, Activin A, and BMP in DMEM/F12 supplemented with 2% BSA (or alternatively HSA), 1 mM L-glutamine, 1% nonessential amino acids, and 0.1 mM 2-mercaptoethanol. Effective amounts of BMP, for example, BMP4, may range from about 1-50 ng/ml, or from about 10 ng/ml to about 50 ng/ml, or about 20 ng/ml to about 80 ng/ml, or about 15 ng/ml, or about 25 ng/ml, or about 50 ng/ml, or about 75 ng/ml, or about 100 ng/ml. Effective amounts of FGF, for example, bFGF, may range from about 10 ng/ml to about 200 ng/ml, or from about 10 ng/ml to about 100 ng/ml, or about 20 ng/ml to about 80 ng/ml, or about 15 ng/ml, or about 25 ng/ml, or about 50 ng/ml, or about 75 ng/ml, or about 100 ng/ml, or about 120 ng/ml, or about 140 ng/ml or about 160 ng/ml, or about 180 ng/ml or about 200 ng/ml. Further, effective amounts of Activin A may range from about 10 ng/ml to about 200 ng/ml, or from about 10 ng/ml to about 100 ng/ml, or about 20 ng/ml to about 80 ng/ml, or about 15 ng/ml, or about 25 ng/ml, or about 50 ng/ml, or about 75 ng/ml, or about 100 ng/ml, or about 120 ng/ml, or about 140 ng/ml or about 160 ng/ml, or about 180 ng/ml or about 200 ng/ml. In one embodiment, FAB medium contains 11 ng/ml bFGF, 100 ng Activin A, and 50 ng BMP4.

ITS medium may include about 5 µg/ml insulin, about 5 µg/ml transferrin, about 5 ng/ml selenous acid, and about 20 to about 100 ng/ml bFGF.

ITSFINE media may include about 5 µg/ml insulin, about 5 µg/ml transferrin, about 5 ng/ml selenous acid (selenium), about 10 ng/ml to about 100 ng/ml FGF7 (R&D), about 50 nM to about 500 nM INGAP (PSN-4765), about 10 mM nicotinamide (Sigma), about 1 nM to about 100 nM exendin-4 (Sigma), about 4 µg/ml to about 15 µg/ml insulin (Gibco), and about 2 g/L BSA (Sigma).

I'IIBEFINE media may include about 150 ng/ml IGF I, about 800 ng/ml IGF II, B27 (50× dilution), about 4 ng/ml insulin, about 10 ng/ml FGF7, about 10 nM exendin-4, and about 10 mM nicotinamide. In some embodiments, 10 uM forskolin and 1 uM ALK5i are included with I'IIBEFINE media.

Growth-factor depleted Matrigel (BD) may be used in the present disclosure as one example of an extracellular matrix that may help cells form three dimensional structures to promote cell-cell contact and create a more islet-like environment. Other extracellular matrix components that form an extracellular matrix gel may be used, including combinations of extracellular matrix components, gelling agents, proteins, and optionally growth factors. For example, combinations of laminins (for example, laminin-411 and laminin-511), collagen IV, entactin, and other polymeric materials may be used. Further, extracellular matrices contemplated may include growth factors such as bFGF, epidermal growth factor, insulin-like growth factor 1, platelet derived growth factor, nerve growth factor, and TGF-β.

Provided herein are multistep cell culture procedures for differentiating stem cells into cell populations comprising pancreatic beta-like cells. In some embodiments, cells are placed in a series of culture conditions (e.g., Stages 1-5), for proscribed time periods. In some embodiments, culture media is changed regularly (e.g., hourly, four-times daily, twice daily, daily, etc.). In some embodiments, culture media is continuously replenished. In some embodiments, cell culture is carried out at room temperature (e.g., 18° C., 19° C., 20° C., 21° C., 22° C., 23° C., 24° C., or ranges therein). In some embodiments, reagents used in culture media are sterilized. In some embodiments, devices (e.g., chambers, vessels, bottles, flasks, tubes, etc.) used in culturing are sterilized.

In some embodiments, appropriate devices are selected for containing cells and media during the various stages of culturing (e.g., Transwell) and/or post-culturing shipping (e.g., conical tube, etc.), clustering (etc., AggreWell), expansion (e.g., Spinner flask, etc.), etc. One commercially available device that finds use in some embodiments described herein are Transwell cell culture chambers, or Transwell plates (e.g., available from Costar Corp., Cambridge, Md., USA). Each chamber of a Transwell plate comprises a flat-bottomed, open-topped, lower compartment with impermeable bottom and sides, and an open-topped, upper compartment with a microporous membrane which forms the bottom of the upper compartment. This assembly is typically covered by a removable lid. In use, cells are placed on the upper surface of the microporous membrane within the upper compartment. The upper compartment is inserted into the lower compartment. Due to the permeability of the membrane, media, nutrients, factors, etc. are able to traverse the membrane.

Additional methods for differentiating iPSCs into a variety of differentiated cell types are described, for example, in Bar-Nur et al., Cell Stem Cell, volume 9, 2011; Takeuchi et al., Scientific Reports 4: 4488 2014; Pagliuca et al., Cell 159, 428-439, Oct. 9, 2014; Rezania et al., Nature Biotechnology, published online 11 Sep. 2014; Mummery et al., Circulation Research. 2012; 111: 344-358; Karumbayaram et al., Stem Cells. 2009 April; 27(4):806-11; Amabile, G. & A. Meissner (2009) Trends Mol. Med. 15:59; U.S. Pat. App. Nos. US20130210141A1; US20130345094A1; U.S. Pat. No. 8,349,609B2; US20140289882A1; US20130259836A1; US20130157358A1; US20130143321A1; and US20110002897A1; each of which is herein incorporated by reference in its entirety.

III. Cellular Analysis

In some embodiments, biochemical and/or molecular analysis is used to compare levels of molecular markers between primary cells, iPSCs, and differentiated cells. The present disclosure is not limited to particular methods of analysis. Examples include but are not limited to, analysis of metabolites, analysis of genomic variations, analysis of cellular proteomes, and analysis of cellular transcriptomes.

The present disclosure is illustrated with mass sequencing and bioinformatics analysis of whole cell transcriptomes. However, the present disclosure is not limited to sequencing analysis or transcription analysis. Additional analysis methods include, but are not limited to, microarray analysis of transcriptomes, protein expression analysis, mass spectroscopy analysis, and chromatography analysis of metabolites.

In some embodiments, analysis methods target genes that are known or suspected of being related to differentiation of the selected cell type. In some embodiments, gene expression markers identified are analyzed on the genomic DNA (e.g., to screen for variations) and protein expression levels. In some embodiments, the whole cell transcriptome, proteome, or metabolome is analyzed.

As indicated, embodiments of the present disclosure provide sequencing and bioinformatics methods for rapidly analyzing and comparing whole cell transcriptomes. The present disclosure is not limited to particular sequencing methods. In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc.

Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In some embodiments, the analysis methods developed by NantWorks (Culver City, Calif.) are utilized to compare gene expression data to identify markers associated with differentiation into a specific differentiate cell type. Exemplary bioinformatics methods are described in U.S. Pat. No. 8,810,598 and U.S. Pat. App. Nos. 20140249847A1, 20140201264A1, and 20140129504A1; each of which is herein incorporated by reference in its entirety.

In some embodiments, gene expression or other molecular analysis data is compared across multiple cell types (e.g., primary cells, iPSCs, and differentiated cells) to identify markers that are specific for differentiation into a particular cell type (e.g. pancreatic beta cells).

IV. Markers

Markers identified using the methods described above find use in a variety of research and clinical applications related to differentiation of iPSCs or embryonic stem cells, as well as screening (e.g., drug screening) and therapeutic (e.g., cell transplantation) applications. For example, in some embodiments, markers are utilized to monitor and/or optimize differentiation methods. In some embodiments, markers are assayed during and after differentiation to monitor progress and determine when differentiation is completed.

In some embodiments, markers are utilized to monitor the safety of differentiated cells (e.g., cells for transplantation into subjects). In some embodiments, markers are identified that are indicative of cells not likely to proliferate uncontrollably (e.g., cells not likely to form tumors or other cancers). Cells are screened prior to transfer to ensure their lack of tumorigenic potential.

In some embodiments, markers fingerprints or patterns comprising levels or presence of multiple markers (e.g., 2, 3, 4, 5, 6, 7, 8, 9, 10 or more markers) are utilized to identify differentiated cells for therapeutic use to insure that cells are therapeutically suitable (e.g., secrete insulin in the case of beta cells), identify cells that are sufficiently differentiated for accurate drug screening, partially differentiated, at a particular stage of differentiation, or uniquely define another cellular state.

In some embodiments, markers are used to screen new differentiation methods or techniques in order to optimize differentiation protocols. In some embodiments, markers associated with differentiation are monitored to compare multiple differentiation methods and select the method that results in differentiated cells that mostly closely match the primary cells.

In some embodiments, detailed gene expression (or other molecule data) is obtained at each stage in the differentiation process and used to alter the differentiation protocol for different starting populations (e.g., cells with varying somatic or genetic profiles). The differentiation process is optimized for different starting populations to ensure that all differentiated cells are uniform in their differentiation.

In some embodiments, markers are utilized in an iterative process to optimize differentiation methods. For example, in some embodiments, one or more differentiation steps are performed and the presence of markers is assayed. In some embodiments, one or more changes in the differentiation process are made, and the marker assay is repeated. The process is repeated as many times as desired (e.g., to optimize differentiation). Thus, the differentiation method are refined iteratively using the markers described herein.

In some embodiments, markers are utilized in drug screening applications. For example, differentiated cells are contacted with a library of compounds useful in the treatment of a given condition and the effect of the compounds on the markers is assayed. Compounds that alter differentiation and/or treat disease can be identified using such methods.

In some embodiments, markers or marker fingerprints are utilized to analyze populations of cells to determine or select the homogeneity of desired cells (e.g., to determine that the population comprises greater than 5%, 10%, 20%, 50%, 75%, 90%, 95%, 99%, or 100% of the desired cells). Such methods are also used, for example, in the purification and isolation of desired cells (e.g., to monitor purification or selection methods).

In some embodiments, populations of cells (e.g., beta-like cells or a cell population comprising beta-like cells) may be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000). In some embodiments, relatively homogeneous cell populations are used in drug screening and therapeutic applications, although heterogeneity in cell populations is also contemplated.

In some embodiments, cells (e.g., beta cells) differentiated and identified using the markers described herein are utilized in therapeutic applications.

For example, provided herein are methods and systems for treating a patient suffering from, or at risk of developing, a conditions or disease (e.g., Type 1 diabetes, Type 2 diabetes, etc.). In certain embodiments, the method involves culturing pluripotent stem cells, differentiating the pluripotent stem cells in vitro into a beta-like cell lineage, and implanting the beta-like cells into the patient.

If appropriate, cells are co-administered with one or more pharmaceutical agents or bioactives that facilitate the survival and function of the transplanted cells. These agents may include, for example, insulin, members of the TGF-β family, including TGF-β 1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-I) and II, GLP-1 and GLP-2 mimetibody, Exendin-4, retinoic acid, parathyroid hormone, MAPK inhibitors, etc.

EXPERIMENTAL

Example 1

Exemplary Methods

Experiments are conducted to de-differentiate and differentiate pancreatic beta cells and identify markers of differentiation.

A. Generation of iPSCs

Islet cells are collected and optionally purified. Retroviral vectors expressing Oct3/4, Klf4, c-Myc, and Sox2 are transfected into the cells. Cells are cultured and passaged for a period of time suitable to induce pluripotency (See e.g., U.S. Pat. No. 8,058,065; herein incorporated by reference in its entirety or other methods described herein).

B. Differentiation of iPSCs iPSCs generated in step A are differentiated into beta cells using the following protocol. Stage 1 Culture Medium
  CDM (Chemical Defined Medium)
  100 ng/ml bFGF (Invitrogen PHG0021)
  100 ng/ml Activin A (R&D 338-AC-050)
  50 ng/ml BMP4 (R&D 314-BP)
CDM:
  100 ml DMEM/F12 (Invitrogen, 11330-057)
  1 ml nonessential amino acids (1% final conc., 1 mM, Invitrogen, 11140)
  1 ml L-glutamine (1% final conc. 2 mM, Invitrogen, 25030-081)
  200 ul 2-mercaptoethanol (final conc. 0.11 mM, Invitrogen, 21985)
Stage 2 Culture Medium (DMEM/F12 (Invitrogen, 11330-057))
  ITS (1000× dilution, BD, 354351)
  50 ng/ml FGF7 (R&D 251-KG-050)
  10 mM Nicotinamide (Sigma, N0636-100 g)
Stage 3 Culture Medium (DMEM/F12 (Invitrogen, 11330-057))
  ITS (1000× dilution, BD, 354351)
  2 uM Retinoic Acid (Sigma, R2625-50MG)
  300 ng/ml Noggin (R&D 6057-NG-100)
  10 mM Nicotinamide (Sigma, N0636-100 g)
Stage 4 Culture Medium (I'IIBFINE+ALK5i+forskolin (DMEM/F12 (Invitrogen, 11330-057)))
  150 ng/ml IGF I (Invitrogen, PHG0078)
  800 ng/ml IGF II (Invitrogen, PHG0084)
  B27 (50× dilution, Gibco, 05-01295A)
  4 ng/ml Insulin (1,000,000× dilution, Gibco, 12585-014)
  10 ng/ml FGF7 (R&D 251-KG-050)
  10 nM exendin-4 (Sigma, E7144-0.1MG)
  10 mM Nicotinamide (Sigma, N0636-100 g)
  1 uM ALK5i II (Calbiochem, 616452)
  25 uM forskolin (Tocris, 1099)
Stage 5 Culture Medium
  150 ng/ml IGF I (Invitrogen, PHG0078)
  10 ng/ml FGF7 (R&D 251-KG-050)
  B27 (50× dilution, Gibco, 05-01295A)
  4 ng/ml Insulin (1,000,000× dilution, Gibco, 12585-014)
  10 nM exendin-4 (Sigma, E7144-0.1MG)
  10 mM Nicotinamide (Sigma, N0636-100 g)
  25 uM forskolin (Tocris, 1099)

The 18-day protocol (ProgenMix III) employs adherent culturing throughout via a Matrigel-coated Transwell platform. To generate definitive endoderm, Stage 1 culture is based on bFGF/Activin A/BMP4 (FAB) treatment of undifferentiated cells in chemically defined, serum-free (3 days of culture with medium changed daily). Subsequently, in stage 2, cells are cultured with insulin-transferrin-selenium (ITS)/FGF7/nicotinamide (3 days of culture with medium changed daily). To promote expansion of pancreatic progenitors, Stage 3 medium is supplemented with ITS/noggin/nicotinamide/retinoic acid (ITSNR; 4 days of culture with medium changed daily). As cell-to-cell contact intensifies, in Stage 4 cells are treated with a cocktail of IGFI/IGFII/B27/FGF7/insulin/nicotinamide/exendin4 (I'IIBFINE) plus ALK5i II and forskolin. In stage 5, cells are then maintained in a media comprising IGFI, IGFII, B27, insulin, nicotinamide, exendin4, and forskolin.

Undifferentiated human induced pluripotent stem cells (hiPSCs) are cultured under standard conditions in stem cell media. Cells should be cultured in a 6 well plate in mTeSR media on Matrigel (1 mg/6 well). Cells are ready for Stage 1 when ~80-90% confluent.

On the day of splitting, a Matrigel coated plate is prepared. One aliquot of growth factor-reduced Matrigel (1 mg/tube) is thawed and diluted with 3 ml cold (4° C.) DMEM/F12. 0.15 ml of diluted Matrigel is added to the plate. The plate sits at room temperature for at least one hour prior to use. Before adding cells, any remaining Matrigel solution is aspirated from the inserts and washed once with PBS. PBS is aspirated and 0.5 ml of mTeSR is added to the lower compartment. The upper compartment is filled with cell suspension.

When undifferentiated cells are 80-90% confluent, they are detached by adding 1 ml of 2 mg/ml dispase to each well. The cells are incubated at 25° C. and observed under microscope until the edges of colonies begin to fold. Dispase is then carefully aspirated. Cells are washed once with PBS.

The cells are collected into a 15 ml conical tube by gently rinsing and scraping with 2 ml of mTeSR. The well is rinsed with an additional 2 ml of mTeSR. The cells are allowed to settle at room temperature to pellet cells. Supernatant is carefully aspirated, and 4 ml mTeSR is added to the pellet and pipet to disperse. Size of clusters/colonies should be ~200-500 um. 0.3 ml of cell suspension is added to the Matrigel coated inserts (prepared above). To distribute the cells evenly the plate is quickly shaken several times in the x and y planes, without swirling. Cells are cultured overnight at 37° C. on incubator rack.

The cells are then examined by microscopy 24 hours after passaging. Two wells of a E-well plate should be sufficient to create a confluent monolayer of cells in the inserts. If there is poor attachment, mTeSR media is changed daily until cells reach 80% confluence.

Stage 1 (Days 0-2)

Spent media is aspirated from both the upper and lower compartments. 0.5 ml of Stage 1 media (CDM, bFGF, Activin A, and BMP4) is added to the lower compartment and 0.3 ml Stage 1 media is added to the upper compartment. Media is exchanged daily and cells are cultured at 37° C. on incubator rack.

Stage 2 (Days 3-5)

On day 3, Stage 2 media (ITS, FGF7, and nicotinamide) is prepared and brought to room temperature. Spent media is aspirated from both the upper and lower compartments. 0.5 ml of Stage 2 media to the lower compartment and 0.3 ml of Stage 2 media is added to the upper compartment. Media is exchanged daily, and between media changes cells are cultured at 37° C. on incubator rack.

Stage 3 (Days 6-9)

On day 6, Stage 3 media (ITS, retinoic acid, Noggin, and nicotinamide) is prepared and brought to room temperature. Spent media is aspirated from both the upper and lower compartments. 0.5 ml of Stage 3 media to the lower compartment and 0.3 ml of Stage 3 media is added to the upper compartment. Media is exchanged daily, and between media changes cells are cultured at 37° C. on incubator rack.

Stage 4 (Days 10-18)

On day 10, Stage 4 media (IGF I, IGF II, B27, insulin, FGF7, exendin-4, nicotinamide, ALK5i II, and forskolin) is prepared and brought to room temperature. Spent media is aspirated from both the upper and lower compartments. 0.5 ml of Stage 4 media to the lower compartment and 0.3 ml of Stage 4 media is added to the upper compartment. Media is exchanged daily, and between media changes cells are cultured at 37° C. on incubator rack.

Stage 5 (Days 19+)

On day 19, Stage 5 media (IGF I, FGF7, B27, insulin, exendin-4, nicotinamide, and forskolin) is prepared and brought to room temperature. Spent media is aspirated from both the upper and lower compartments. 0.5 ml of Stage 5 media to the lower compartment and 0.3 ml of Stage 5 media is added to the upper compartment. Media is exchanged daily, and between media changes cells are cultured at 37° C. on incubator rack.

C. Identification of Markers

Gene expression is analyzed by performing RT-PCR or qPCR followed by next generation sequencing methods or RNA-SEQ. A computer processor and computer software is used to compare gene expression of primary islet (beta) cells, iPSCs obtained from the islet cells, and beta cells differentiated from the iPSCs. Markers of differentiation are those that are unique to primary and differentiated beta cells. Markers are validated at the DNA or protein level in vitro or in situ.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A method of identifying differentiation markers expressed in pancreatic β-cell lineage cells, comprising:
 (a) culturing an isolated primary cell under conditions that comprise exogenously expressing Oct4, Sox2, cMyc, and Klf4 in said primary cell, such that said primary cell de-differentiates to generate an induced pluripotent stem cell (iPSC);
 (b) treating said iPSC under conditions such that said iPSC differentiates into a pancreatic β-cell, wherein said treating comprises:
  (i) culturing the iPSC in a chemically defined medium comprising fibroblast growth factor, Activin A and bone morphogenetic protein,
  (ii) culturing the cells produced from step (i) in the presence of chemically defined medium comprising insulin, transferrin, selenium, a fibroblast growth factor and nicotinamide,
  (iii) culturing the cells produced from step (ii) in the presence of a chemically defined medium comprising insulin, transferrin, selenium, retinoic acid, a bone morphogenetic protein inhibitor and nicotinamide;
  and (iv) culturing the cells produced from step (iii) in the presence of a serum-free medium comprising an insulin-like growth factor, insulin, nicotinamide, exendin-4 and/or GLP-1, a TGF-β inhibitor, and an agent that increases cAMP; and (c) identifying molecular markers expressed during differentiation, wherein said markers are indicative of differentiation of said iPS cell into a pancreatic β-cell.

2. The method of claim 1, wherein said primary cell is a pancreatic beta cell.

3. The method of claim 1, wherein said culturing in step (a) further comprises expanding said cell.

4. The method of claim 1, wherein said culturing in step (a) further comprises inducing expression of one or more genes selected from the group consisting of nanog, LIN28, and Glis1.

5. The method of claim 1, further comprising:
(d) maintaining the cells of the pancreatic lineage for 1-50 days by culturing the cells from step (c) in the presence of a serum-free medium, an insulin-like growth factor, fibroblast growth factor, insulin, nicotinamide, exendin-4 and/or GLP-1, and an agent that increase cAMP.

6. The method of claim 1, wherein the fibroblast growth factor of step (b) is basic fibroblast growth factor (bFGF).

7. The method of claim 1, wherein the bone morphogenetic protein of step (b) is BMP4.

8. The method of claim 1, wherein the chemically defined medium comprising insulin, transferrin, and selenium of steps (b) and/or step (c) is ITS medium.

9. The method of claim 1, wherein the fibroblast growth factor of step (b) is FGF7.

10. The method of claim 1, wherein the bone morphogenetic protein inhibitor of step (b) is a BMP4 inhibitor.

11. The method of claim 1, wherein the serum-free medium of step (b) is B27.

12. The method of claim 1, wherein the primary and differentiated cells are the same or different cell types.

13. The method of claim 1, wherein step (a) has a duration of 2-10 days.

14. The method of claim 1, wherein said identifying comprises sequencing expressed genes in said primary cell, said iPSC, and said pancreatic β-cell and comparing said expressed genes to identify gene expression markers indicative of differentiation into said pancreatic β-cell.

15. The method of claim 14, wherein said comparing comprises the use of bioinformatics methods.

* * * * *